United States Patent [19]

Tang et al.

[11] Patent Number: 5,358,836

[45] Date of Patent: * Oct. 25, 1994

[54] PHOTOGRAPHIC ELEMENTS CONTAINING NEW MAGENTA-DYE-FORMING TRIS COUPLERS

[75] Inventors: Ping-Wah Tang; Philip T. S. Lau; Stanley W. Cowan, all of Rochester, N.Y.

[73] Assignee: Eastman Kodak Company, Rochester, N.Y.

[*] Notice: The portion of the term of this patent subsequent to Aug. 23, 2011 has been disclaimed.

[21] Appl. No.: 169,465

[22] Filed: Dec. 17, 1993

[51] Int. Cl.$^5$ ................................ G03C 7/38
[52] U.S. Cl. ................................. 430/548; 430/381
[58] Field of Search ........................ 430/381, 548

[56] References Cited

U.S. PATENT DOCUMENTS

| | | | |
|---|---|---|---|
| 4,540,654 | 9/1985 | Sato et al. | 430/385 |
| 4,621,046 | 11/1986 | Sato et al. | 430/381 |
| 5,139,931 | 8/1992 | Seto et al. | 430/548 |

FOREIGN PATENT DOCUMENTS 61-169846  7/1986  Japan .

Primary Examiner—Richard Schilling
Attorney, Agent, or Firm—Joshua G. Levitt

[57] ABSTRACT

The invention provides new magenta-dye-forming couplers, new magenta dyes formed therefrom, and new photographic elements containing the new couplers. The new couplers have the structure (I):

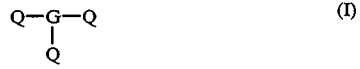

wherein

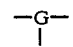

has the structure (II)

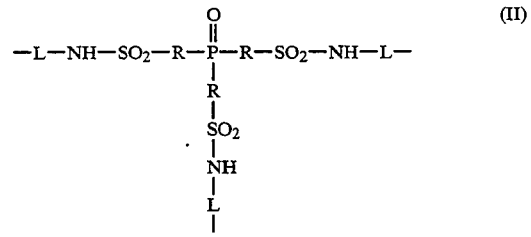

wherein each —R— is independently a substituted or unsubstituted alkylene, alkoxylene, arylene, or aryloxylene group, and each —L— is independently a substituted or unsubstituted alkylene, alkoxylene, arylene, aryloxylene, or aryloxyalkylene group, and Q— has the structure (III):

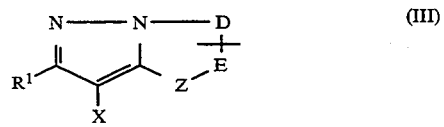

wherein: each R$^1$— is independently H— or a substituent;

each X— is independently H— or a coupling-off group; and each of D, E, and Z is independently a substituted or unsubstituted methine group, =N—, or —NH—, with the provisos that one of either the D—E or the E—Z bonds is a double bond and the other is a single bond, and when the D—E bond is a carbon-carbon double bond it may form part of an aromatic ring fused with Q—, and one of D, E, and Z is a methine group bonded to

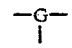

8 Claims, No Drawings

PHOTOGRAPHIC ELEMENTS CONTAINING NEW MAGENTA-DYE-FORMING TRIS COUPLERS

FIELD OF THE INVENTION

This invention relates to new dye-forming couplers and new magenta dyes formed therefrom and to photographic silver halide elements containing such new couplers. More particularly, the invention concerns new magenta-dye-forming tris couplers comprising three bicyclic pyrazoloazole coupling moieties bonded to a phosphorous-containing linking group.

BACKGROUND

Color images are commonly obtained in the silver halide photographic art by reaction between the development product of a silver halide developing agent (e.g., oxidized aromatic primary amine developing agent) and a color forming compound commonly referred to as a coupler. The reaction between the coupler and oxidized developing agent results in coupling of the oxidized developing agent to the coupler at a reactive site on the coupler, known as the coupling position and yields a dye. The subtractive process of color formation is ordinarily employed in color photographic elements, and the dyes produced by coupling are usually cyan, magenta, or yellow dyes which are formed in or adjacent to silver halide emulsion layers sensitive to red, green, or blue radiation, respectively.

Couplers well known for forming magenta dyes include, e.g., pyrazolones and bicyclic pyrazoloazoles, as described, for example, in U.S. Pat. Nos. 3,725,067; 3,810,761; 4,443,536; 4,540,654; and 4,621,046.

However, such known couplers often have drawbacks. One such drawback is too much undesirable absorption of red and/or blue light in addition to the desired absorption of green light. This can result when the dye formed by the coupling reaction exhibits significant spectral absorption over a wider than desirable range of wavelengths of radiation. This is commonly referred to in terms of the dye's having a larger than desirable bandwidth. A smaller bandwidth means the dye absorbs less significant amounts of radiation outside the region of desired absorption, i.e., in the case of a magenta dye desired to absorb only green light, less significant undesired absorption of the longer red and-/or shorter blue radiation wavelengths.

Another con, non drawback is the relatively high equivalent weight of many magenta couplers. The term, "equivalent weight", as used herein is equal to the molecular weight of the coupler divided by the number of efficiently reactive coupling moieties in the coupler molecule. Each efficiently reactive coupling moiety is capable of reacting with oxidized developing agent to form a colored dye moiety. The higher the equivalent weight of the coupler is, the larger is the mass of coupler that must be included in a photographic element layer in order to be able to produce the desired amount of developed image dye optical density. The need for a larger mass of coupler in a layer results in a thicker layer, which inherently reduces the transparency and optical sharpness of the layer. Thus, lower equivalent weight couplers allow for thinner, more transparent, optically sharper layers. Unfortunately, the overall mass of a coupler molecule must be relatively large in order to provide sufficient organic ballast to properly suspend the coupler molecules in droplets of high boiling organic liquid, referred to as coupler solvent, which are dispersed in the desired layer of the photographic element, and thereby anchor the coupler in the layer and prevent it from diffusing to adjacent layers or out of the element during processing with various aqueous processing liquids. Thus, the needs for lower equivalent weight and sufficient organic ballast are at apparent cross-purposes.

Also, some charactersitics of pyrazoloazole magenta-dye-forming couplers are significantly affected by the nature of any particular substituents that may be bonded to the coupling moieties at their coupling position. For example, it is known that the nature of such substituents can have a significant effect on how quickly and efficiently a coupling moiety can couple with oxidized developing agent at the coupling position to form a dye moiety, because such substituents must detach from the coupling position during the coupling reaction. Furthermore, after detachment from the coupling position, such substituents can remain in a photographic element along with the dye produced by the coupling reaction, and it is known that the nature of such detached substituents can then significantly affect the stability of the dye produced and can also significantly affect other components or activity in the photographic element, e.g., the rate of further development by developing agents.

There is therefore a continuing need for a new class of magenta-dye-forming couplers that can minimize the drawbacks described above, i.e., that can form dyes exhibiting relatively small bandwidths and that have relatively low equivalent weight, while at the same time having relatively high molecular weight to provide sufficient organic ballast for proper incorporation and anchoring in photographic element layers. It would also be desirable for such a new class of couplers to provide the flexibility to choose among various different substituents to have at the coupling position of the coupling moieties of such couplers, in order to be able to tailor the effects of such substituents (effects such as described above) to meet particular needs in various photographic elements. Of course, the couplers should also exhibit all the other characteristics desirable for good photographic performance.

SUMMARY OF THE INVENTION

The present invention meets the above-noted need by providing new magenta-dye-forming couplers, new magenta dyes formed therefrom, and new photographic elements containing the new couplers.

The new magenta-dye-forming couplers provided by the invention are tris coupler compounds having the structure (I):

(I)

wherein

has the structure (II)

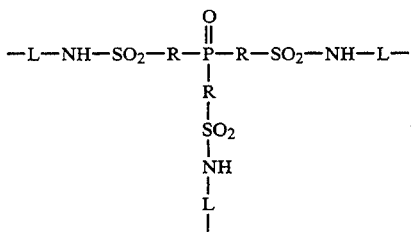

wherein each —R— is independently a substituted or unsubstituted alkylene, alkoxylene, arylene, or aryloxylene group, and each —L— is independently a substituted or unsubstituted alkylene, alkoxylene, arylene, aryloxylene, or aryloxyalkylene group, and Q— has the structure (III):

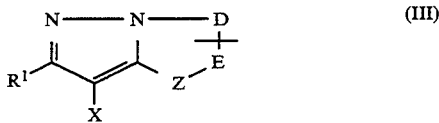

wherein: each $R^1$— is independently H— or a substituent;

each X— is independently H— or a coupling-off group; and each of D, E, and Z is independently a substituted or unsubstituted methine group, =N—, or —NH—, with the provisos that one of either the D—E or is a the E—Z bonds is a double bond and the other is a single bond, and when the D—E bond is a carbon-carbon double bond it may form part of an aromatic ring fused with Q—, and one of D, E, and Z is a methine group bonded to

The new magenta dyes of the invention are the dyes that are formed by coupling reaction of an oxidized photographic color developing agent and the new tris couplers of the invention.

The photographic elements of the invention each comprise a support having thereon a photographic silver halide emulsion layer and one or more of the new tris couplers of the invention.

The couplers, dyes, and photographic elements of the invention provide a number of advantages.

The new dyes formed by the new couplers have been unexpectedly found to exhibit relatively small bandwidths, and thus cause less undesirable absorption of radiation in the red and blue wavelength regions.

Couplers of the invention have relatively low equivalent weight, because each coupler molecule contains three efficiently reactive coupling moieties of structure (III) bonded to a central linking group of structure (II). Thus the equivalent weight of the couplers of the invention is only one third of their molecular weight, and layers in photographic elements of the invention containing such couplers can be made thinner and thus more transparent and optically sharper.

Conversely, the three coupling moieties plus linking group in couplers of the invention result in the couplers' having relatively high molecular weights, which easily provide sufficient organic ballast to properly suspend the coupler molecules in coupler solvent and anchor them in layers of photographic elements of the invention.

Also, because the linking group of structure (II) in couplers of the invention is bonded to the coupling moieties of structure (III) at a position other than the coupling position, the new class of magenta-dye-forming couplers of the invention provides the flexibility to choose among various different substituents (represented by X— in structure (III)) to have at the coupling position of the coupling moieties. Thus, one is able to tailor the effects of such substituents (e.g., effects on coupling speed and efficiency, effects on dye stability, effects on other components and activity in a photographic element, etc.) to meet particular needs in various photographic elements of the invention.

Furthermore, it was unpredictable that inclusion of the phosphorous-containing linking group of structure (II) in the coupler molecules would still yield couplers having the other characteristics necessary or desirable for good photographic performance. The couplers of the invention have been unexpectedly found to have such characteristics. For example, the inventive couplers are compatible with common coupler solvents and are efficiently reactive with oxidized photographic color developing agents to form dye and, when incorporated in silver halide photographic elements, provide good photographic speed. The inventive magenta dyes formed by the couplers afford high maximum density (Dmax) and contrast and good peak spectral absorptivity at desired wavelengths in the green spectral region, and images formed by such dyes in photographic elements of the invention exhibit good thermal, hydrolytic, chemical, and light stabilities. The couplers and dyes of the invention do not adversely interact with other common components that may be included in photographic elements of the invention.

DESCRIPTION OF PREFERRED EMBODIMENTS

All the Structure (I) couplers of the invention contain the phosphorous-containing tris linking group of structure (II) above.

Each coupler molecule of the invention also contains three coupling moieties, each bonded to the tris linking group through a different one of each of the three free bonds shown in Structure (II) above. The particular coupling moieties employed are chosen depending upon the hue and other characteristics desired to be imparted to any particular photographic element of the invention.

In magenta-dye-forming couplers of the invention the coupling moieties in the coupler molecules have the structure (III) above.

In more preferred embodiments of magenta-dye-forming couplers of the invention the coupling moieties in the coupler molecules have the structure (IV):

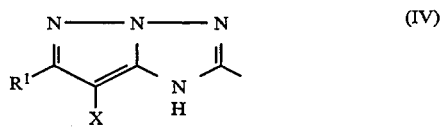

wherein R¹— and X— are as previously defined for Structure (III), and the coupling moiety is bonded to the tris linking group through connection of the free bond shown in Structure (IV) to one of the three free bonds shown in Structure (II).

As used herein, the terms "substituent" and "substituted" are meant to denote a wide range of various groups which can be chosen, as is well known in the art, depending upon the effect or lack of effect desired on various characteristics of the couplers, e.g., solubility, diffusion resistance, dye hue, dye stability, etc. Such groups include, for example: halo, e.g., chloro, bromo or fluoro; nitro; hydroxyl; cyano; and carboxyl and its salts; and groups which may be further substituted, such as alkyl, including straight or branched chain alkyl, such as methyl, trifluoromethyl, ethyl, t-butyl, 3-(2,4-di-t-amylphenoxy) propyl, and tetradecyl; alkenyl, such as vinyl and 2-butenyl; alkoxy, such as methoxy, ethoxy, propoxy, butoxy, 2-methoxyethoxy, sec-butoxy, hexyloxy, 2-ethylhexylocy, tetradecyloxy 2-(2,4-di-t-pentylphenoxy) ethoxy, and 3-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; amido, such as acetamido, benzamido, butyramido, tetradecanamido, alpha-(2,4-di-t-pentyl-phenoxy) acetamido, alpha-(2,4-di-t-pentylphenoxy)butyramido, alpha-(3- pentadecylphenoxy)-hexanamido, alpha-(4-hydroxy-3-t-butylphenoxy)-tetradecanamido, 2-oxopyrrolidin-1-yl, 2-oxo-5-tetradecyl-pyrrolin-1-yl, N-methyltetradecanamido, N-succinimido, N-phthalimido, 2,5-dioxo-1-oxazolidinyl, 3-dodecyl-2, 5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl) carbonylamino, p-dodecylphenylcarbonylamino, p-toluylcarbonylamino, N-methylureido, N,N-dimethylureido, N-methyl-N-dodecylureido, N-hexadecylureido, N, N-dioctadecylureido, N,N-dioctyl-N'-ethylureido, N-phenylureido, N,N-diphenylureido, N-phenyl-N-p-toluylureido, N-(m-hexadecylphenyl)ureido, N,N-(2,5-di-t-pentylphenyl)-N'-ethylureido; and t-butylcarbonamido; sulfonamido, such as methylsulfonamido, benzenesulfonamido, p-toluylsulfonamido, p-dodecylbenzenesulfonamido, p-toluylsulfonamido, p-dodecylbenzenesulfonamido, N-methyltetradecylsulfonamido, N,N-dipropylsulfamoylamino, and hexadecylsulfonamido; sulfamyl, such as N-methylsulfamyl, N-ethylsulfamyl, N,N-dipropylsulfamyl, N-hexadecylsulfamyl, N, N-dimethylsulfamyl, N-[3-(dodecyloxy)propyl]sulfamyl, N[4-(2,4-di-t-pentylphenoxy)butyl]sulfamyl, N-methyl-N-tetradecylsulfamyl, and N-dodecylsulfamyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxytDhenoxycarbonyl methoxycarbonyl butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-toluylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-toluylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amino, such as phenylanilino, 2-chloroanilino, diethylamino, dodecylamino; imino, such as 1 (N-phenylimido) ethyl, N-succinimido or 3-benzylhydantoinyl; azo, such as phenylazo and naphthylazo; a heterocyclic group, heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and siloxy, such as trimethylsiloxy.

The particular substituents used may be selected to attain the desired photographic properties for a specific application and can include, for example, hydrophobic groups, solubilizing groups, blocking groups, etc. Generally, the above groups and substituents thereof may typically include those having 1 to 42 carbon atoms and typically less than 30 carbon atoms, but greater numbers are possible depending on the particular substituents selected. Moreover, as indicated, the substituents may themselves be suitably substituted with any of the above groups.

The term "alkyl" or "alkylene" standing alone herein or as part of another term is meant to denote $C_1$-$C_{20}$ alkyl or alkylene.

The term "aryl" or "arylene" standing alone herein or as part of another term is meant to denote $C_6$–$C_{12}$ or arylene.

Suitable "coupling-off groups" such as represented by "X" at the coupling position in Structures (III) and (IV) herein are known to those skilled in the art. Such groups can determine the equivalency of the coupler, can modify the reactivity of the coupler, or can advantageously affect the layer in which the coupler is coated or other layers in the element by performing, after release from the coupler, such functions as development inhibition, development acceleration, bleach inhibition, bleach acceleration, color correction, and the like. Representative classes of coupling-off groups include halo, particularly chloro, bromo, or fluoro; alkoxy; aryloxy; heterocyclyloxy; heterocyclic, such as hydantoin and pyrazolyl groups; sulfonyloxy; acyloxy; amido; imido; acyl; heterocyclylimido; thiocyano; alkylthio; arylthio; heterocyclylthio; sulfonamido; phosphonyloxy; and arylazo. They are described, for example, in U.S. Pat. Nos. 2,355,169; 3,227,551; 3,432,521; 3,476,563; 3,617,291; 3,880,661; 4,052,212 and 4,134,766; the disclosures of which are hereby incorporated herein by reference.

Examples of specific coupling-off groups are Cl, F, Br, —SCN, OCH$_3$, —OC$_6$H$_5$, —OCH$_2$C(=O)NHCH$_2$CH$_2$OH, —OCH$_2$C (=O) NHCH$_2$CH$_2$OCH$_3$, —OCH$_2$C (=O) NHCH$_2$CH$_2$OC (=O) OCH$_3$, —NHSO$_2$CH$_3$, —OC (=O) C$_6$H$_5$, —NHC(=O) C$_6$H$_5$, OSO$_2$CH$_3$, —P(=O) (OC$_2$H5)$_2$, —S(CH$_2$)$_2$CO$_2$H,

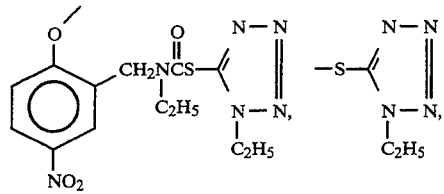

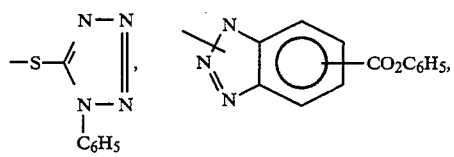

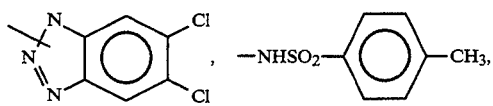

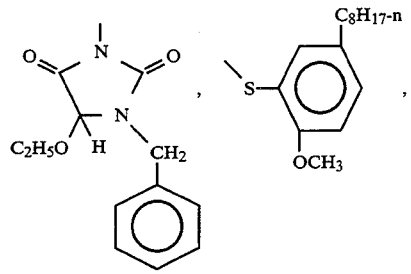

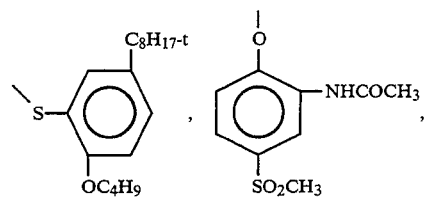

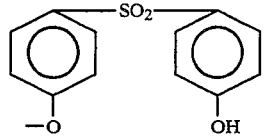

and

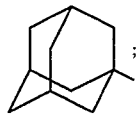

In particularly preferred embodiments of magenta-dye-forming couplers of the invention containing three coupling moieties of Structure (III) above, bonded to a tris linking group of Structure (II) above: each —R— is independently phenylene or phenoxylene; each —L— is independently propylene or phenoxytrimethylene; each $R^1$— is independently substituted or unsubstituted alkyl, with particularly preferred specific examples being methyl, t-butyl, or and each X— is independently halo or a substituted or unsubstituted aryloxy, arythio, or nitrogen-containing heterocyclic group, with particularly preferred specific examples being chloro, 1-pyrazolyl, phenoxy, or phenylthio.

Some specific examples of magenta-dye-forming couplers of the invention are illustrated in Table I, showing the tris linking group of Structure (II) and the three coupling moieties of Structure (IV) which together comprise each coupler molecule.

TABLE I

| Coupler | Tris Linking Group | Coupling Moieties |
|---|---|---|
| M-1 | (structure) | (structure with (CH₃)₃C) |
| M-2 | (structure) | (structure with adamantyl) |

TABLE I-continued

| Coupler | Tris Linking Group | Coupling Moieties |
|---|---|---|
| M-3 | | |
| M-4 | | |

TABLE I-continued

| Coupler | Tris Linking Group | Coupling Moieties |
|---|---|---|
| M-5 | (structure with phosphate linking three phenyl-SO₂-NH-CH₂-CH(CH₃)- groups) | (pyrazolotriazole-type structure with Cl, (CH₃)₃C, and NH substituents) |

TABLE I-continued

| Coupler | Tris Linking Group | Coupling Moieties |
|---|---|---|
| M-6 | (structure with phosphate triester linking three sulfonamide-phenyl groups) | (chloro-pyrazolotriazole-type moiety with adamantyl substituent) |
| M-7 | (structure with phosphine oxide linking three sulfonamide-phenyl groups) | (chloro-pyrazolotriazole-type moiety with tert-butyl substituent) |

TABLE I-continued

| Coupler | Tris Linking Group | Coupling Moieties |
|---|---|---|
| M-8 | | |
| M-9 | | |
| M-10 | | |

TABLE I-continued
| Coupler | Tris Linking Group | Coupling Moieties |
|---|---|---|
| M-11 | 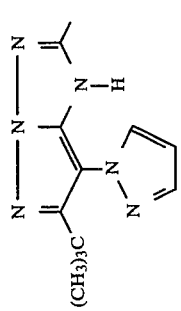 | 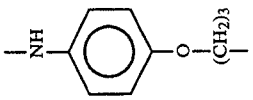 |

Couplers of the invention can be readily prepared by known general condensation reactions starting with appropriate known derivatives of the coupling moieties and linking group. One convenient general scheme is as follows, wherein D, E, Z, R$^1$—, X—, —L—, and —R— are as described in regard to Structures (II) and (III) above.

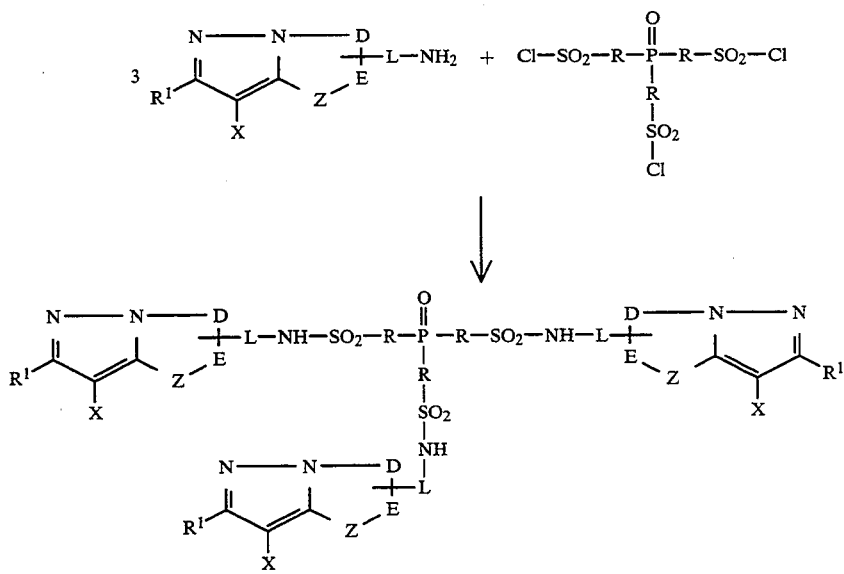

A working example of a specific preparation of a specific coupler of the invention is as follows:

Preparation Example: Coupler M-4 of Table I

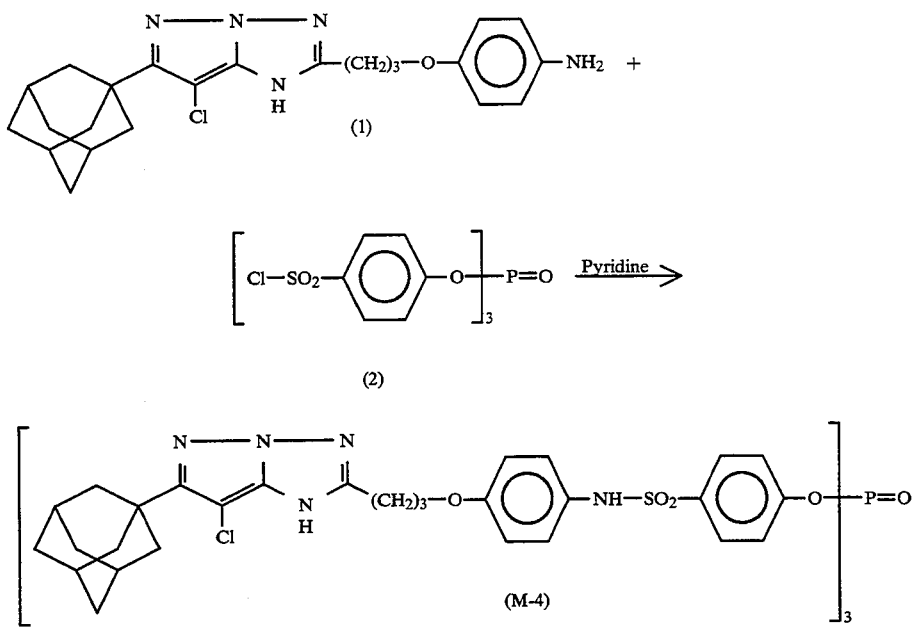

To a stirred solution of 5.11 g (0.012 mole) of (1) in 25 mL of pyridine at room temperature was added 2.49 g (0.004 mol) of chlorosulfonylphenyl phosphate (2). After being stirred under nitrogen for 13 h, the reaction mixture was slowly poured into a mixture of ice and water containing 30 mL of concentrated hydrochloric acid. Filtration of the mixture afforded 7 g of crude product (M-4). Flash chromotography (silica gel, elu-tion with gradient of 20–50% AcOEt/ligroin) yielded 4.30 g (60%) of tris coupler (M-4) as a white solid. Physical, combustion analysis and spectroscopic data are consistent with the assigned structure.

Dyes in accordance with the invention are those formed by well-known coupling reaction of an oxidized photographic color developing agent with a coupler, in this case a coupler in accordance with the invention.

The photographic elements of the invention each comprise a support having thereon a photographic silver halide emulsion layer and one or more of the new tris couplers of the invention. Such elements can contain any of the layers and components known in the photographic art, with at least one of the magenta-dye-forming couplers therein being a coupler of this invention.

Couplers of the invention can be used in any of the ways and in any of the combinations in which couplers are used in the photographic art. Many such ways and combinations are well known to those in the photographic art. Typically, the coupler is incorporated in a silver halide emulsion and the emulsion is coated on a support to form a photographic element of the invention. Alternatively, the coupler can be incorporated in an element of the invention at a location adjacent to the silver halide emulsion where, during development, the coupler will be in reactive association with development products such as oxidized color developing agent. Thus, as used herein, the term "associated" signifies that the coupler is in the silver halide emulsion layer or in an adjacent location where, during processing, the coupler is capable of reacting with silver halide development products.

The photographic elements of the invention can be single color elements or multicolor elements. Multicolor elements contain dye-image-forming units sensitive to each of the three primary regions of the spectrum. Each unit can comprise a single emulsion layer or multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer.

A typical multicolor photographic element of the invention comprises a support bearing a cyan-dye-image-forming unit comprising at least one red-sensitive silver halide emulsion layer having associated therewith at least one cyan-dye-forming coupler, a magenta-dye-image-forming unit comprising at least one green-sensitive silver halide emulsion layer having associated therewith at least one magenta-dye-forming coupler, and a yellow-dye-image-forming unit comprising at least one blue-sensitive silver halide emulsion layer having associated therewith at least one yellow-dye-forming coupler, at least one of the magenta-dye-forming couplers in the element being a coupler of this invention. The element can contain additional layers, such as filter layers, interlayers, overcoat layers, subbing layers, and the like.

If desired, the photographic element can be used in conjunction with an applied magnetic layer as described in *Research Disclosure,* November 1992, Item 34390 published by Kenneth Mason Publications, Ltd., Dudley Annex, 12a North Street, Emsworth, Hampshire P010 7DQ, ENGLAND.

In the following discussion of some suitable materials for use in the emulsions and elements of this invention, reference will be made to *Research Disclosure,* Issue Number 908, December 1989, Item 308119, pages 993–1015, available as described above, which will be identified hereafter by the term "Research Disclosure." The contents of the Research Disclosure, including the patents and publications referenced therein, are incorporated herein by reference, and the Sections hereafter referred to are Sections o#the Research Disclosure.

The silver halide emulsions employed in the elements of this invention can be either negative-working or positive-working. Some suitable emulsions and their preparation as well as methods of chemical and spectral sensitization are described in Sections I through IV. Color materials and development modifiers are described in Section IX, and various additives such as brighteners, antifoggants, stabilizers, light absorbing and scattering materials, hardeners, coating aids, plasticizers, lubricants and matting agents are described, for example, in Sections V, VI, VIII, X, XI, XII, and XVI. Manufacturing methods are described in Sections XIV and XV, other layers and supports in Sections XIII and XVII, processing methods and agents in Sections XIX and XX, and exposure alternatives in Section XVIII.

Preferred supports are paper, cellulose acetate, and poly(ethylene terephthalate).

Photographic elements can be exposed to actinic radiation, usually in the visible region of the spectrum, to form a latent image and then processed to form a visible dye image. Processing to form a visible dye image includes the step of contacting the element with a color developing agent to reduce developable silver halide and oxidize the color developing agent. Oxidized color developing agent in turn reacts with the coupler to yield a dye of the invention.

Preferred color developing agents are p-phenylenediamines. Especially preferred are:

4-amino N,N-diethylaniline hydrochloride,
4-amino-3-methyl-N,N-diethylaniline hydrochloride
4-amino-3-methyl-N-ethyl-N-(b-(methanesulfonamido)ethyl)aniline sesquisulfate hydrate,
4-amino-3-methyl-N-ethyl-N-(b-hydroxyethyl)aniline sulfate,
4-amino-3-b-(methanesulfonamido)ethyl-N,N-diethylaniline hydrochloride, and
4-amino-N-ethyl-N-(2-methoxyethyl)-m-toluidine di-p-toluene sulfonic acid.

With negative working silver halide this processing step leads to a negative image. To obtain a positive (or reversal) image, this step can be preceded by development with a non-chromogenic developing agent to develop exposed silver halide, but not form dye, and then uniformly fogging the element to render the unexposed silver halide developable. Alternatively, a direct positive emulsion can be employed to obtain a positive image.

Development is followed by the conventional steps of bleaching, fixing, or bleach-fixing, to remove silver and silver halide, washing and drying.

The following examples are presented to further illustrate some specific photographic elements of the invention containing couplers of the invention.

Comparative examples are also provided containing couplers outside the scope of the present invention. Comparative couplers employed are as follows:

Comparative Magenta-Dye Forming Coupler C-1:

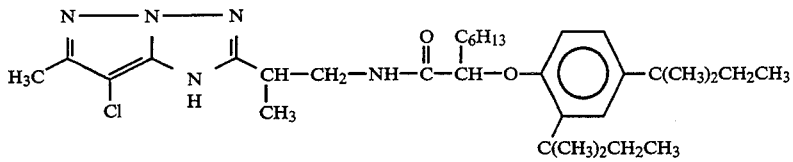

Comparative Magenta-Dye Forming Coupler C-2:

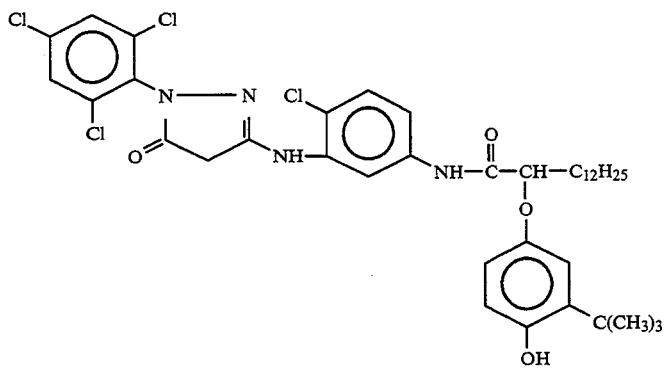

EXAMPLES 1–3 AND COMPARATIVE EXAMPLES A–B

Preparation of Photographic Elements

Dispersions of the couplers were prepared in the following manner: The quantities of each component are found in Table II. In one vessel the coupler, stabilizer (2,2′,3,3′-tetrahydro-3,3,3′,3′-tetramethyl-5,5′,6,6′-tetrapropoxy-1,1′-spirobi[1H-indene]), coupler solvent (diethyl dodecanamide), and ethyl acetate were combined and warmed to dissolve. In a second vessel, gelatin, Alkanol XC ™ (surfactant and Trademark of E. I. DuPont Co., U.S.A.) and water were combined and warmed to about 40° C. The two mixtures were mixed together and passed three times through a Gaulin colloid mill. The ethyl acetate was removed by evaporation and water was added to restore the original weight after milling.

TABLE II

| Dispersion Number | Coupler Number | Grams Coupler | Grams Stabilizer | Grams Coupler Solvent | Grams Ethyl Acetate | Grams 12.5% Gelatin | Grams Alkanol XC (10%) | Grams Water |
|---|---|---|---|---|---|---|---|---|
| 1 | M-1 | 0.643 | 0.322 | 0.965 | 1.930 | 19.20 | 2.40 | 14.54 |
| 2 | M-2 | 0.743 | 0.372 | 1.115 | 2.230 | 19.20 | 2.40 | 13.94 |
| 3 | M-4 | 0.764 | 0.382 | 1.146 | 2.292 | 19.20 | 2.40 | 13.82 |
| A | C-1 | 0.733 | 0.366 | 1.098 | 2.198 | 19.20 | 2.40 | 14.00 |

Dispersion B was composed of comparison coupler C-2 (8.73% by weight), 3,4-dihydro-2,2-dimethyl-4-(1-methylethyl-7-octyl-2H-benzopyran-6-ol (3.714%), 2,5-di-sec-dodecylhydroquinone (0.873%), dibutyl phthalate (4.454%), and gelatin (8.69%).

The photographic elements were prepared by coating the following layers in the order listed on a resin-coated paper support:

| | |
|---|---|
| 1st Layer | |
| Gelatin | 3.23 g/m² |
| 2nd Layer | |
| Gelatin | 1.61 g/m² |
| Coupler Dispersion | 4.3 × 10⁻⁴ mole coupling moieties/m² |
| AgCl emulsion | 0.17 g Ag/m² and green-sensitized |
| 3rd Layer | |
| Gelatin | 1.33 g/m² |
| 2-(2H-benzotriazol-2-yl)-4,6-bis-(1,1-dimethylpropyl)phenol | .73 g/m² |
| Tinuvin 326 ™ (Ciba-Geigy) | 0.13 g/m² |
| 4th Layer | |
| Gelatin | 1.40 g/m² |
| Bis(vinylsulfonylmethyl)ether | 0.14 g/m² |

Exposing and Processing of Photographic Elements

The photographic elements were given stepwise exposures to green light and processed as follows at 35°0C.

| | |
|---|---|
| Developer | 45 seconds |
| Bleach-Fix | 45 seconds |
| Wash (running water) | 90 seconds |

The developer and bleach-fix were of the following compositions:

| Developer | |
|---|---|
| Water | 700.00 mL |
| Triethanolamine | 12.41 g |
| Blankophor REU ™ (Mobay Corp.) | 2.30 g |
| Lithium polystyrene sulfonate (30) | 0.30 g |
| N,N-Diethylhydroxylamine (85%) | 5.40 g |
| Lithium sulfate | 2.70 g |
| N-{2-[4-amino-3-methylphenyl)ethylamino]ethyl}-methanesulfonamide, susquisulfate | 5.00 g |
| 1-Hydroxyethyl-1,1-diphosphonic acid (60%) | 0.81 g |
| Potassium carbonate, anhydrous | 21.16 g |
| Potassium chloride | 1.60 g |
| Potassium bromide | 7.00 g |
| Water to make | 1.00 L |
| pH at 26.7° C., adjusted to 6.7 | |
| Bleach-Fix | |
| Water | 700.00 mL |
| Solution of Ammonium thiosulfate (56.4%) plus Ammonium sulfite (4%) | 127.40 g |
| Sodium metabisulfite | 10.00 g |
| Acetic acid (glacial) | 10.20 g |
| Solution of Ammonium ferric ethylene-diaminetetraacetate (44%) + Ethylenediamine-tetraacetic acid (3.5%) | 110.40 g |
| Water to make | 1.00 L |

-continued pH @ 26.7° C. adjusted to 6.7

Photographic Tests

Magenta dyes were formed upon processing. The following photographic characteristics were determine: D-max (the maximum density to green light); D-min (the minimum density to green light); Lambda-max (the wavelength of peak absorption at a density of 1.0); and Bandwidth (the width of the absorption spectrum in manometers at half the peak density). These values for each example are tabulated in Table III.

TABLE III

| Example Number | Dispersion | Coupler | D-max | D-min | Lambda-max | Bandwidth |
|---|---|---|---|---|---|---|
| 1 | 1 | M-1 | 2.59 | 0.07 | 548 | 96 |
| 2 | 2 | M-2 | 2.48 | 0.09 | 549 | 95 |
| 3 | 3 | M-4 | 2.48 | 0.09 | 548 | 94 |
| Comp. A | A | C-1 | 2.39 | 0.10 | 543 | 105 |
| Comp. B | B | C-2 | 2.51 | 0.09 | 540 | 106 |

The equivalent weight advantage of the couplers of the invention is illustrated in Table IV.

TABLE IV

| Coupler Number | Molecular Weight | Equivalent Weight |
|---|---|---|
| M-1 | 1508 | 503 |
| M-3 | 1556 | 519 |
| C-1 | 572 | 572 |
| C-2 | 779 | 779 |

The data from Tables III and IV show that the tris-magenta couplers of this invention coated at levels proportional to their equivalent weights provide dyes with narrower bandwidths than those obtained from the comparison examples.

The lower equivalent weights of the couplers of the present invention allow a reduction in coating load, resulting in thinner coating for improving transparency and optical sharpness of the layer.

The invention has been described in detail with particular reference to certain preferred embodiments thereof, but it should be appreciated that variations and modifications can be effected within the spirit and scope of the invention.

What is claimed is:

1. A photographic element comprising a support having thereon a photographic silver halide emulsion layer and a magenta-dye-forming tris coupler having the structure:

wherein

has the structure

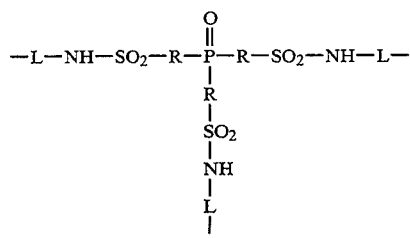

wherein each —R— is independently a substituted or unsubstituted alkylene, alkoxylene, arylene, or aryloxylene group, and each —L— is independently a substituted or unsubstituted alkylene, alkoxylene, arylene, aryloxylene, or aryloxyalkylene group, and Q— has the structure:

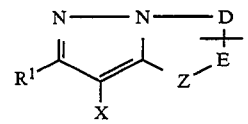

wherein: each $R^1$— is independently H— or a substituent;

each X— is independently H— or a coupling-off group; and each of D, E, and Z is independently a substituted or unsubstituted methine group, =N—, or —NH—, with the provisos that one of either the D—E or the E—Z bonds is a double bond and the other is a single bond, and when the D—E bond is a carbon-carbon double bond it may form part of an aromatic ring fused with Q—, and one of D, E, and Z is a methine group bonded to

2. The photographic element of claim 1, wherein Q— has the structure:

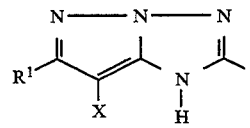

wherein $R^1$— and X— are as defined in claim 1.

3. The photographic element of claim 1, wherein each —R— is independently phenylene or phenoxylene.

4. The photographic element of claim 1, wherein each —L— is independently propylene or phenoxytrimethylene.

5. The photographic element of claim 1, wherein each $R^1$— is a substituted or unsubstituted alkyl group.

6. The photographic element of claim 1, wherein each $R^1$— is independently methyl or t-butyl or has the structure:

7. The photographic element of claim 1, wherein each X— is independently halo or a substituted or unsubstituted aryloxy, arythio, or nitrogen-containing heterocyclic group.

8. The photographic element of claim 1, wherein each X— is independently chloro, 1-pyrazolyl, phenoxy, or phenylthio.

* * * * *